United States Patent
Li et al.

(10) Patent No.: US 7,544,212 B2
(45) Date of Patent: *Jun. 9, 2009

(54) BONE IMPLANT COMPOSITE

(75) Inventors: Shu-tung Li, Oakland, NJ (US); Debbie Yuen, Woodcliff Lake, NJ (US); Hui-chen Chen, Wayne, NJ (US)

(73) Assignee: Collagen Matrix, Inc., Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/029,095

(22) Filed: Feb. 11, 2008

(65) Prior Publication Data

US 2008/0138381 A1 Jun. 12, 2008

Related U.S. Application Data

(63) Continuation-in-part of application No. 11/635,824, filed on Dec. 8, 2006, now Pat. No. 7,381,224.

(51) Int. Cl.
*A61F 2/36* (2006.01)
(52) U.S. Cl. .................................. 623/23.51
(58) Field of Classification Search ............... 623/23.51
See application file for complete search history.

(56) References Cited

U.S. PATENT DOCUMENTS

| 4,795,467 | A | 1/1989 | Piez et al. |
| 5,231,169 | A | 7/1993 | Constantz et al. |
| 5,455,231 | A | 10/1995 | Constantz et al. |
| 5,573,771 | A | 11/1996 | Geistlich et al. |
| 5,776,193 | A | 7/1998 | Kwan et al. |
| 6,187,047 | B1 | 2/2001 | Kwan et al. |

FOREIGN PATENT DOCUMENTS

EP 0309241 3/1989

OTHER PUBLICATIONS

Chen et al., "A Collagen-Anorganic Bone Composite for Bone Repair: Part I. In Vitro Characterization Studies," Transactions of the 31$^{st}$ Annual Meeting of the Society of Biomaterials, vol. XXIX (Apr. 2006).
Speer et al., "A Collagen-Anorganic Bone Composite for Bone Repair: Part II: In Vivo Study in a Rabbitt Radius Defect Model," Transactions of the 31$^{st}$ Annual Meeting of the Society of Biomaterials, vol. XXIX (Apr. 2006).

*Primary Examiner*—Maryam Monshipouri
(74) *Attorney, Agent, or Firm*—Occhiuti Rohlicek & Tsao LLP

(57) ABSTRACT

A bone implant composite comprising a collagen matrix and a calcium-based mineral, the calcium-based mineral having a particle size of 25-2000 μm and being interspersed in the collagen matrix; wherein the bone implant composite contains 3-60% by weight the collagen matrix and 40-97% by weight the calcium-based mineral, and has a pore size of 50-500 μm, a density range of 0.02-0.8 g/cm$^3$, a tensile strength range of 0.4-100 kg/cm$^2$, and a compression modulus range of 0.2-10 kg/cm$^2$. Also disclosed are methods of preparing the above-described composite.

17 Claims, No Drawings

BONE IMPLANT COMPOSITE

CROSS-REFERENCE TO RELATED APPLICATIONS

This application is a continuation-in-part of U.S. application Ser. No. 11/635,824, filed Dec. 8, 2006 now U.S. Pat. No. 7,381,224, and titled "Bone Implant Composite," The contents of this application is incorporated herein by reference.

BACKGROUND

Collagen implants can be used in orthopedic tissue and dental repair. It is preferred to include synthetic or natural calcium-based mineral in the implants to increase bone conductivity, i.e., growth of bone cells. See, e.g., U.S. Pat. No. 6,846,853. Mechanical strength is an important consideration in designing such collagen-mineral implants as there is a need for securely affixing them to target sites.

SUMMARY

In one aspect, the present invention features a porous bone implant composite including a collagen matrix and calcium-based mineral. The calcium-based mineral, such as anorganic bone mineral and carbonate apatite, has a particle size of 25-2000 μm (e.g., 30-1000 μm) and is interspersed in the collagen matrix. This bone implant composite contains 3-60% (e.g., 5-55% or 20-40%) by weight the collagen matrix and 40-97% (e.g., 55-95% or 60-80%) by weight the calcium-based mineral. It has a pore size of 50-500 μm (e.g., 50-200 μm or 150-500 μm), a density range of 0.02-0.8 g/cm$^3$ (e.g., 0.03-0.7 g/cm$^3$), and a tensile strength range of 0.4-100 kg/cm$^2$ (e.g., 0.5-10 kg/cm$^2$). Further, the hydrated composite has a compression modulus range of 0.2-10 kg/cm$^2$ (e.g., 0.4-8.0 kg/cm$^2$ or 0.6-5.0 kg/cm$^2$). As an example, a bone implant composite contains 45% by weight the collagen matrix and 55% by weight anorganic bone mineral having a particle size of 30-150 μm; and has a pore size of 150-500 μm, a density of 0.035-0.055 g/cm$^3$, a tensile strength of 0.5-0.8 kg/cm$^2$, and a compression modulus of 0.5-0.8 kg/cm$^2$.

In another aspect, the present invention features a method of preparing a bone implant composite. The method includes dispersing collagen fibers and calcium-based mineral in an acidic or basic aqueous solution to form a suspension, adjusting the pH value of the suspension so as to coacervate the collagen fibers, freeze-drying the suspension to form a dried mixture, and contacting the dried mixture with a crosslinking agent to crosslink the collagen fibers.

In still another aspect, the present invention features a method similar to that described above, except that the pH adjusting step is omitted and the calcium-based mineral is anorganic bone mineral, carbonate apatite, or a mixture thereof.

The details of one or more embodiments of the invention are set forth in the description below. Other features, objects, and advantages of the invention will be apparent from the description and from the claims.

DETAILED DESCRIPTION

As described above, the bone implant composite of this invention contains a collagen matrix and calcium-based mineral.

The collagen matrix is preferably prepared from type I, type II or type III collagen fibers. In particular, type I collagen fibers from humans, animals, or from genetically engineered methods are most preferred. Type I collagen fibers can be isolated and purified from type I collagen-rich tissues such as skin, tendon, ligament, and bone of humans and animals. The methods of isolation and purification of collagen fibers have been described in Methods in Enzymology, vol. 82, pp. 33-64, 1982; in The Preparation of Highly Purified Insoluble Collagen, Oneson, I., et al., Am. Leather Chemists Assoc., Vol. LXV, pp. 440-450, 1970; and in U.S. Pat. No. 6,090,996. Genetically engineered collagen fibers such as those marketed by Fibrogen (South San Francisco, Calif.). As well known in the art, collagen fibers, at or near their isoelectric point, reconstitute and aggregate into longer fibers, which completely separate from the solution phase. This process is called coacervation. Depending on how they are prepared, different collagen fibers have different isoelectric points. In the bone implant composite of this invention, the collagen matrix can be made of either coacervated or non-coacervated collagen fibers.

The calcium-based mineral preferably has a particle size of 25-2000 μm, more preferably 30-1000 μm. It can be synthetic or naturally occurring calcium-containing substance that are suitable for medicinal use. Examples include, but are not limited to calcium phosphate, calcium sulfate, calcium carbonate, anorganic bone mineral, and carbonate apatite. Anorganic bone mineral is derived from bone (e.g., bovine cancellous and cortical bone) by removing organic constituents. See, e.g., *Implant Dent.* 2001, 10 (2): 139-42. Preferably, it contains about 5-7% carbonate. Carbonate apatite is apatite that contains carbonate ions. See, e.g., *Journal of Materials Science: Materials in Medicine,* 1998, 9 (12): 779-83. The carbonate content of the carbonate apatite preferably ranges from 2 to 12%.

The bone implant composite of this invention can be prepared by the following steps: (1) dispersing the above described collagen fibers and calcium-based mineral in an acidic or basic aqueous solution to form a suspension, (2) freeze-drying the suspension to form a dried mixture, and (3) contacting the dried mixture with a crosslinking agent to crosslink the collagen fibers. Each of these steps are described in detail below.

(1) Dispersing

Collagen fibers and calcium-based mineral are dispersed in an acidic or basic aqueous solution to obtain a suspension. The weight ratio of the collagen fibers and calcium-based mineral typically ranges from 3:97 to 60:40 and the suspension typically has a solid content of 0.02 to 0.8 g/ml. To achieve a uniform mixing, one can homogenize the collagen-mineral suspension by a commercially available homogenizer (e.g., Silverson Homogenizer), a blender, or a mixer.

One can use various acidic or basic solutions, e.g., $C_2H_5COOH$ or HCl solution having a pH of 1.5-4 or NaOH or KOH solution having a pH of 10.5-13.5, to disperse collagen fibers and calcium-based mineral. It is preferred that the pH of the solution be different from the isoelectric point of the collagen fibers.

The collagen fibers swell upon contact with the acidic or basic solution. The swelling leads to a low density and a low compression modulus of the bone implant composite prepared from these collagen fiber. The extent of the swelling depends on, among others, dispersing time and the pH value of the solution. For example, an acidic solution facilitates swelling better than a basic solution. Thus, if a low-density bone implant composite of this invention is desired, one can use an acidic solution to achieve greater swelling of collagen fibers.

Calcium-based mineral and collagen fibers can be simultaneously or sequentially dispersed in an acidic or basic solution. Calcium-based mineral gradually dissolve in acid. Thus, when an acidic solution is used, it is preferred that the calcium-based mineral is dispersed after the collagen fibers so as to avoid substantial lose of the mineral.

After a collagen-mineral suspension is obtained, one can optionally coacervate the collagen fibers to obtain longer fibers by adjusting the pH of the suspension to the isoelectric point of the collagen fibers (e.g., pH of 4.5-5.5). Either a base or an acid can be used to coacervate the collagen fibers, depending on the pH of the suspension. The lengths of coacervated fibers in their extended conformation can be measured by a ruler. If the desired lengths have not been achieved, vacuum can be applied to the suspension to remove trapped air bubbles that dampen the coacervation. This process can be repeated until the fibers have the desirable lengths. See U.S. Ser. No. 10/971,435.

It has been observed that swollen collagen fibers are coacervated better. Thus, if coacervation is needed, it is preferred that an acid solution, a better swelling agent than a basic solution, be used in the dispersing step.

Coacervated collagen fibers have greater mechanical strength than non-coacervated collagen fibers. In addition, as coacervated collagen fibers are longer than non-coacervated collagen fibers, a bone implant made of coacervated collagen fibers is more dense than a bone implant obtained made of non-coacervated collagen fibers.

Finally, a suspension of collagen fibers (either coacervated or non-coacervated) and calcium-based mineral thus obtained is neutralized, if necessary, by a base or acid to bring its pH value within 7±3 (preferably 7±2, and more preferably 7±1).

(2) Freeze-drying

The just-described collagen-mineral suspension is then freeze-dried. As an example, a 250 ml of suspension is frozen at −40° C. and dried at −20° C. for about 24 to 48 hours and finally at 20° C. for about 8-24 hours under vacuum at about 100 millitorr. After frozen water is removed, the spaces that it occupied become pores. As a result, a porous dried collagen-mineral mixture is formed. One can prepare a bone implant having a desired pore size and, in turn, a desired density by controlling the amount of water prior to the freeze-drying process. For example, one can partially remove water from the suspension in order to afford a bone implant having a small pore size and a high density. Various methods may be used to remove water. If coacervation has been performed, the coacervated collagen fibers are separated from the solution and one can remove water by decanting, squeezing, centrifuging, and filtering. For a suspension containing non-coacervated collagen fibers, one can centrifuge the suspension and then remove a desirable volume of the supernatant.

(3) Cross-linking

The freeze-dried collagen-mineral mixture thus obtained is then subjected to a cross-linking reaction, in which the collagen fibers are covalently bonded to each other via a suitable cross-linking agent (e.g., an aldehyde compound) to give a bone implant composite. The dried mixture can be brought in contact with a vapor generated from a solution containing a cross-linking agent, the extent of cross-linking being controlled by the vapor pressure, the solution temperature, and the reaction time. Methods for determining the extent of cross-linking are well known in the art, e.g., by monitoring the hydrothermal transition temperature or by determining the number of intermolecular cross-linking points. See Yuen, et al., *Trans. Soc. Biomaterials,* 1288, 2000 and Wiederhorn, et al., *J. Polymer Sci.,* 9:315, 1952.

The bone implant composite may be made of various shapes (e.g., strip or pad) by placing collagen-mineral suspensions in different molds and then freezing the suspension in the molds. To prepare granular implant composites, one can first prepare a sheet of a dried collagen-mineral mixture, cross-link the collagen fibers, and then break the sheet into granules.

The above-described bone implant composite can be used in orthopedic tissue repair. For example, it can be used in filling bone voids or gaps of the skeletal system, e.g., extremities, spine, and pelvis. It can be provided as a sterile, dry material to be hydrated with autogenous bone marrow at the point of use. Strip and pad implants can be cut into shapes to fit a defective bone site and are designed to retain their shape and physical integrity following implantation in a site. Granular implants can be compacted to obtain a pre-designed shape.

The bone implant composite of this invention can be used in either dry or hydrated form. The hydrated composite can made by, e.g., immersing the dry composite in water for 5 minutes. The hydrated composite thus-prepared has a compression modulus range of 0.01-0.5 kg/cm$^2$ (e.g., 0.02-0.4 kg/cm$^2$ or 0.03-0.2 kg/cm$^2$).

The collagen-mineral composite of this invention may contain one or more growth factors, such as bone morphogenetic proteins, platelet derived growth factors, transforming growth factors, and bone marrows. It may also include other bioactive agents such as anti-microbial agents. The bioactive agents can be attached to the collagen-mineral matrix via mechanical interactions, electrostatic interactions or covalent bonding. Alternatively, they can be incorporated into a collagen-mineral matrix via physical interactions or diffusion mechanism.

Further, the collagen-mineral composite may contain cells, such as osteoblasts, stem cells, chondrocytes, sertoli cells, and blood and marrow-based cells. To introduce cells into the collagen-mineral matrix, one can seed cells on the top of the matrix and allow cells to infiltrate into the pores of the matrix. Alternatively, one can directly inject the cells into the pores via a needle. The cells incorporated in the matrix may be allowed to culture in vitro prior to in vivo implantation.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

1.5 g of type I collagen fibers and 1.5 g of anorganic bone mineral (particle size of 30-150 μm) were uniformly mixed in a 200 ml beaker. The collagen fibers were prepared essentially in the same manner as that disclosed in U.S. Pat. No. 6,716,225. The anorganic bone mineral, derived from bovine femur bone by removing organic substances, was a commercialized product, i.e., NuOss™ (ACE Surgical Supply, Inc.; particle size: 250-1000 μm).

To the above mixture was slowly added 100 ml of 0.01 M NaOH aqueous solution. After several hours of agitation, the mixture was homogenized by a mixer (Stephen Mill) for 1 minute, de-aired under vacuum, and then poured into a 24 cm×50 cm stainless steel tray and freeze-dried. The freeze-dried collagen anorganic bone composite was crosslinked with formaldehyde vapor generated from 0.5% formaldehyde solution for 4 hours at ambient temperature to obtain a collagen-mineral composite.

The mineral content, pore size, density, tensile strength, and compression modulus of the collagen-mineral composite were measured by the methods described below:

1. Mineral Content

The mineral content of a collagen-mineral composite was calculated by deducting the weight of collagen from the total weight of the composite. The weight of collagen was obtained by first determining the weight of hydroxyproline and then converting this weight into the weight of collagen containing 14% by weight hydroxyproline.

2. Pore Size

The pore size was measured using scanning electron micrographs. Briefly, a collagen-mineral composite sample was cut in the cross-section and fixed. A micrograph was taken at a certain magnification (e.g., ×100). The pore size was determined as the longest distances of pores.

3. Density

A collagen-mineral composite sample was first dried under vacuum or over $P_2O_5$ for 24 hours. Its weight was recorded. Its volume was calculated from its dimensions (i.e., the length, width, and thickness), which were measured using a caliper. The density was determined as weight/volume in unit of $g/cm^3$.

4. Tensile Strength

A sample was cut into a dumbbell shape by a die punch and soaked in phosphate buffered saline (pH 7.4) at 25° C. for about 2 minutes. It was then secured to a clamp fixture and pulled at a speed of 1.0 in/min by a mechanical tester (Chatillon, Greensboro, N.C.) until it broke. The tensile strength was recorded.

The collagen-mineral composite prepared in this example had a 45:55 weight ratio of collagen to anorganic bone mineral, a pore size of 50-200 μm, and a density of 0.04 $g/cm^3$, and a tensile strength of 0.67±0.13 $kg/cm^2$.

5. Compression Modulus

The compression modulus of the collagen-mineral composite was measured using a Chatillon TCD200 mechanical tester equipped with a compression platform test stand that includes a pair of compression plates. The measurement was conducted as follows:

A 1 cm×1 cm sample of the collagen-mineral bone implant composite, dry or hydrated (immersed in water for 5 minutes), was placed between the compression plates. The sample was compressed at a rate of 1.25 cm/min to the half height of its original thickness. The peak compression modulus ($kg/cm^2$) was recorded. The results show that the dry composite had a compression modulus of 0.75 $kg/cm^2$ and the hydrated composite has a compression modulus of 0.04 $kg/cm^2$.

Example 2

1.25 g of collagen fibers was dispersed in 200 ml 0.07 M lactic acid solution (pH 2.3) overnight. 1.25 g of anorganic bone mineral (particle size 200-500 μm) was then added. The collagen fibers were prepared essentially in the same manner as that disclosed in U.S. Pat. No. 6,716,225. The anorganic bone mineral was obtained by grinding and meshing NuOss™ (ACE Surgical Supply, Inc.), which has a particle size of 250-1000 μm.

The dispersion was homogenized with a Silverson homogenizer for 1 minute and de-aired under vacuum. The pH of the dispersion was adjusted to coacervate the collagen fibers. The resultant mixture was de-aired under vacuum, partially dehydrated by decanting the solution to reduce the volume to 160 ml, poured into a 12 cm×20 cm stainless steel tray, and then freeze-dried. The freeze-dried mixture was crosslinked in formaldehyde vapor generated from 0.5% formaldehyde solution for 4 hours at ambient temperature to afford a collagen-mineral composite.

The mineral content, pore size, density, and tensile strength of the collagen-mineral composite thus prepared were measured according to the methods described in Example 1. It had a 50:50 weight ratio of collagen to mineral, a pore size of 50-150 μm and a density of 0.09 $g/cm^3$, a tensile strength of 8.17±1.24 $kg/cm^2$.

A 1 cm×1 cm sample of the collagen-mineral bone implant composite, dry or hydrated (immersed in water for 5 minutes), was placed between the compression plates. The sample was compressed at a rate of 1.25 cm/min to the half height of its original thickness. The peak compression modulus ($kg/cm^2$) was recorded. The results show that the dry composite had a compression modulus of 1.43 $kg/cm^2$ and the hydrated composite has a compression modulus of 0.04 $kg/cm^2$.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A bone implant composite comprising a swollen, freeze-dried and crosslinked collagen matrix and a calcium-based mineral, the calcium-based mineral having a particle size of 25-2000 μm and being interspersed in the collagen matrix; wherein the bone implant composite contains 3-60% by weight the collagen matrix and 40-97% by weight the calcium-based mineral, and has a pore size of 50-500 μm, a density range of 0.02-0.8 $g/cm^3$, a tensile strength range of 0.4-100 $kg/cm^2$, and a compression modulus range of 0.2 to 10 $kg/cm^2$.

2. The bone implant composite of claim 1, wherein the particle size of the calcium-based mineral is 30-1000 μm.

3. The bone implant composite of claim 1, wherein the bone implant composite contains 5-55% by weight the collagen matrix and 45-95% by weight the calcium-based mineral.

4. The bone implant composite of claim 3, wherein the bone implant composite contains 20-40% by weight the collagen matrix and 60-80% by weight the calcium-based mineral.

5. The bone implant composite of claim 1, wherein the bone implant composite has a pore size of 150-500 μm.

6. The bone implant composite of claim 1, wherein the bone implant composite has a density range of 0.03-0.7 $g/cm^3$.

7. The bone implant composite of claim 1, wherein the bone implant composite has a tensile strength range of 0.5-10 kg/cm$^2$.

8. The bone implant composite of claim 1, wherein the calcium-based mineral is anorganic bone mineral.

9. The bone implant composite of claim 1, wherein the calcium-based mineral is carbonate apatite.

10. The bone implant composite of claim 9, wherein the carbonate content of the carbonate apatite ranges from 2 to 12%.

11. The bone implant composite of claim 1, wherein the composite has a compression modulus range of 0.6 to 5.0 kg/cm$^2$.

12. The bone implant composite of claim 1, wherein the composite has a compression modulus of 0.5-0.8 kg/cm$^2$.

13. The bone implant composite of claim 1, wherein the calcium-based mineral is anorganic bone mineral and has a particle size of 30-1000 μm; and the bone implant composite contains 5-55% by weight the collagen matrix and 45-95% by weight the anorganic bone mineral, and has a pore size of 150-500 μm, a density range of 0.03-0.7 g/cm$^3$, a tensile strength range of 0.5-10 kg/cm$^2$, and a compression modulus range of 0.6 to 5.0 kg/cm$^2$.

14. The bone implant composite of claim 13, wherein the bone implant composite contains 20-40% by weight the collagen matrix and 60-80% by weight the calcium-based mineral.

15. The bone implant composite of claim 1, wherein the calcium-based mineral is anorganic bone mineral and has a particle size of 30-150 μm; and the bone implant composite contains 45-55% by weight the collagen matrix and 45-55% by weight the anorganic bone mineral, and has a pore size of 150-500 μm, a density of 0.035-0.055 g/cm$^3$, a tensile strength of 0.5-0.8 kg/cm$^2$, and a compression modulus of 0.5-0.8 kg/cm$^2$.

16. The bone implant composite of claim 1, wherein the calcium-based mineral is carbonate apatite and has a particle size of 30-1000 μm; and the bone implant composite contains 5-55% by weight the collagen matrix and 45-95% by weight the carbonate apatite, and has a pore size of 50-200 μm, a density range of 0.03-0.7 g/cm$^3$, a tensile strength range of 0.5-10 kg/cm$^2$, and a compression modulus range of 0.6 to 5.0 kg/cm$^2$.

17. The bone implant composite of claim 16, wherein the bone implant composite contains 20-40% by weight the collagen matrix and 60-80% by weight the calcium-based mineral.

* * * * *